United States Patent
Oda et al.

(10) Patent No.: US 6,342,627 B1
(45) Date of Patent: Jan. 29, 2002

(54) PRODUCING UNSATURATED ESTERS BY A LANTHANIDE METAL ALKOXIDE CATALYZED TRANSESTERIFICATION PROCESS

(75) Inventors: Yoshiaki Oda, Toyonaka; Makoto Yako, Takatsuki; Kazunori Iwakura, Ibaraki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/459,919

(22) Filed: Dec. 14, 1999

(30) Foreign Application Priority Data

Dec. 17, 1998 (JP) ............................. 10-359042

(51) Int. Cl.$^7$ ............................................... C07C 67/02
(52) U.S. Cl. ........................................................ 560/217
(58) Field of Search ......................................... 560/217

(56) References Cited

FOREIGN PATENT DOCUMENTS

| JP | 46485 B | 1/1971 |
| JP | 56104851 A | 8/1981 |

*Primary Examiner*—Gary Geist
*Assistant Examiner*—Robert W. Deemie
(74) *Attorney, Agent, or Firm*—Birch, Stewart, Kolasch & Birch, LLP

(57) ABSTRACT

There is disclosed a process for producing an unsaturated ester of the formula (3):

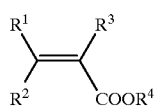

(3)

wherein $R^1$, $R^2$ and $R^3$ independently represent hydrogen, halogen, alkyl, alkenyl and the like and $R^5$ represents alkyl which may be substituted and the like, which process is characterized by subjecting an unsaturated ester of the formula (1):

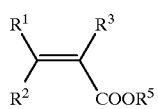

(1)

wherein $R^1$, $R^2$ and $R^3$ have the same meaning as previously defined and $R^4$ represents alkyl or phenyl and the like, to a transesterification reaction with a hydroxy compound of the formula (2):

$$R^5OH \qquad (2)$$

wherein $R^5$ has the same meaning as previously defined, in the presence of a lanthanoide metal alkoxide.

11 Claims, No Drawings

PRODUCING UNSATURATED ESTERS BY A LANTHANIDE METAL ALKOXIDE CATALYZED TRANSESTERIFICATION PROCESS

FIELD OF THE INVENTION

The present invention relates to process for producing unsaturated esters.

DESCRIPTION OF THE RELATED ART

There has been known alkali metal alkoxides disclosed in U.S. Pat. No. 2,744,884 and organotin compounds disclosed in Japanese Patent Application Kokai (Laid-Open) No. 56-104851 as catalysts for accelerating transesterification reactions. For the synthesis of unsaturated esters, these catalysts, however, had a drawback in that they required vigorous reaction conditions accompanied by side reactions such as polymerization of unsaturated esters and addition of substrate alcohols to the unsaturated esters.

SUMMARY OF THE INVENTION

An object of the invention is to provide a transesterification process for producing unsaturated esters, which process can be conducted under less vigorous conditions and is not accompanied by undesirable side reactions.

The present invention provides a process for producing an unsaturated ester of the formula (3):

(3)

where $R^1$, $R^2$ and $R^3$ independently represent:
  a hydrogen atom, a halogen atom,
  an alkyl group which may be substituted,
  an alkenyl group which may be substituted,
  an aralkyl group which may be substituted or
  an aryl group which may be substituted; and
$R^5$ represents:
  an alkyl group which may be substituted with an alkoxy group, a phenoxy group, a cyano group, a dialkylamino group, a cycloalkyl group or a halogen atom,
  an aralkyl group which may be substituted with an alkyl group, an alkoxy group, a phenoxy group, a nitro group, a cyano group or a halogen atom, or
  an aryl group which may be substituted with an alkyl group, an alkoxy group or a halogen atom;
which comprises:
  subjecting an unsaturated ester of the formula (1):

(1)

where $R^1$, $R^2$ and $R^3$ have the same meaning as defined above and
$R^4$ represents an alkyl group having 1 to 10 carbon atoms which may be substituted or a phenyl group which may be substituted, to a transesterification reaction with a hydroxy compound of the formula (2):

$$R^5OH \qquad (2)$$

wherein $R^5$ has the same meaning as defined above, in the presence of a lanthanoide metal alkoxide.

DESCRIPTION OF THE PREFERRED EMBODIMENTS

The present invention is described in detail below.

In the present invention preferably used catalysts include at least one lanthanoide alkoxide selected from alkoxide compounds of La, Ce, Pr, Nd, Pm, Sm, Eu, Gd, Tb, Dy, Ho, Er, Tm, Yb and Lu, as a catalyst, and more preferred are the alkoxide compounds of La and Sm, which are industrially readily available.

Polymers of the lanthanum alkoxide may be also used in addition to monomers depending on the type of the metal or the aliphatic hydrocarbon groups.

Examples of the lanthanoide metal alkoxide include compounds of the formula (4):

$$Ln(OR^6)(OR^7)(OR^8) \qquad (4)$$

wherein Ln is a lanthanoide metal element and $R^6$, $R^7$ and $R^8$ are the same or different and represent an alkyl group having 1 to 10 carbon atoms.

$R^6$, $R^7$ and $R^8$ may be an alkyl group having 1 to 10 carbon atoms which may be straight-chained, branched or cyclic, and the alkyl groups may bond together at their terminals to form a divalent or trivalent alkoxide residue they may combine to form a 2-or 3-valent alkoxide. Examples thereof include methyl, ethyl, n-propyl, i-propyl, n-butyl, i-butyl, t-butyl, n-pentyl, n-hexyl, n-octyl, cyclopropyl, cyclobutyl, cyclopentyl and cyclohexyl.

Methoxides, ethoxides, n-propoxides, i-propoxides, t-butoxides and the like are preferably used as the alkoxide because of their easy preparation. More preferably, n-propoxides, i-propoxides and t-butoxides are used because of their good solubility in the solvent listed below. Still more preferably, i-propoxides are used because of their low costs for the catalyst preparation and their advantages in the preparation operations.

The lanthanoide metal alkoxide (2) can be prepared by known methods and they may be isolated after preparation thereof and then used in the present process or used directly as solutions without being isolated after their preparation.

The lanthanoide metal alkoxide may be contacted with a hydroxy compound (2) and then the resulting compound may be used in the present transesterification reaction.

The amount of the lanthanoide metal alkoxide to be used is not particularly limited. It is usually 0.001–200 mole %, preferably 0.01–20 mole % per mol of the unsaturated ester (1).

After completion of the transesterification reaction, the lanthanoide metal alkoxide can be recovered by removing the solvent and product, for example, by distillation and/or filtration.

The recovery of the catalyst compound can be facilitated by using a supported lanthannoid metal alkoxide, for example, on a polymer, silica gel, or active carbon, alternatively the lanthanoide alkoxide can be microencapsulated with resins by conventional methods, thereby reuse of the recovered catalyst can be improved.

The unsaturated esters used as a starting material in the present invention are compounds of the formula (1). In the formula, $R^1$, $R^2$ and $R^3$ independently represent:

a hydrogen atom, a halogen atom, an alkyl group which may be substituted, an alkenyl group which may be substituted, an aralkyl group which may be substituted or an aryl group which may be substituted.

Examples of the alkyl group which may be substituted include a straight or branched or cyclic alkyl group having 1 to 10 carbon atoms which may be substituted with at least one group selected from a halogen atom(e.g., fluorine, chlorine, bromine and iodine), and $(C_1–C_3)$alkoxy group (e.g., methoxy, ethoxy, n-propoxy, and i-propoxy).

Specific examples thereof include methyl, ethyl, n-propyl, i-propyl, n-butyl, s-butyl, t-butyl, n-pentyl, n-hexyl, cyclohexyl, menthyl, chloromethyl, dichloromethyl, trichloromethyl, bromomethyl, dibromomethyl, tribromomethyl, 1-chloroethyl, 2-chloroethyl, 1-bromoethyl, 2-bromoethyl, 1,2-dichloroethyl, 1,2-dibromoethyl, 2,2,2-trichloroethyl, 2,2,2-tribromoethyl, methoxymethyl and 2-methoxyethyl.

Examples of the alkenyl group which may be substituted include a straight or branched or cyclic alkenyl group having 2 to 10 carbon atoms which may be substituted with at least one group selected from a halogen atom(e.g., fluorine, chlorine, bromine and iodine) and $(C_1–C_3)$ alkoxy group (e.g., methoxy, ethoxy, n-propoxy, and i-propoxy).

Specific examples of the alkenyl group include vinyl, 1-methylvinyl, 1-propenyl, 2-methyl-l-propenyl, 2,2-dichlorovinyl, 2,2-dibromovinyl, 2-chloro-2-fluorovinyl, 2-chloro-2-trifluoromethylvinyl and 2-bromo-2-tribromomethylvinyl.

Examples of the aralkyl which may be substituted include benzyl, diphenylmethyl, phenylethyl, naphthylmethyl and naphthylethyl, all of which may be substituted on their aromatic ring with at least one group selected from a $(C_1–C_{10})$alkyl group described above, a $(C_1–C_6)$alkoxyl group(e.g., methoxy, ethoxy, n-propoxy, i-propoxy, n-butoxy, s-butoxy, t-butoxy and cyclohexoxy) and a halogen atom and the like.

Examples of the aryl group which may be substituted include phenyl, 1-naphthyl and 2-naphthyl, and all of which may be substituted on their aromatic rings with at least one group selected from the above-mentioned $(C_1–C_{10})$alkyl group, $(C_1–C_6)$alkoxyl group, a halogen atom and the like.

In the formula (1), $R^4$ represents an alkyl group having 1–10 carbon atoms or a phenyl group which may be substituted. Examples of the alkyl group having 1–10 carbon atoms may be the same groups as exemplified for $R^6$, $R^7$ and $R^8$. Examples of the phenyl group which may be substituted include a phenyl group which may be substituted with at least one group selected from the same $(C_1–C_{10})$alkyl groups, $(C_1–C_6)$alkoxyl groups and the halogen atoms as described above.

Specific examples of the unsaturated esters (1) include:

methyl acrylate, methyl crotonate, methyl methacrylate, methyl tiglate, methyl 3,3-dimethylacrylate, methyl 2-pentenoate, methyl 2-fluoroacrylate, methyl 3,3-dichloroacrylate, methyl 4,4-dichlorocrotonate, methyl 2-dichloromethylacrylate, methyl 5,5-dichloropenta-2,4-dienate, methyl 3-benzylacrylate, methyl 2-benzylacrylate, methyl 2-(p-methylbenzyl)acrylate, methyl 2-(p-methoxybenzyl)acrylate, methyl 2-(p-chlorobenzyl)acrylate, methyl cinnamate, methyl p-methylcinnamate, methyl p-methoxycinnamate, methyl p-chlorocinnamate, ethyl acrylate, ethyl crotonate, ethyl methacrylate, ethyl tiglate, ethyl 3,3-dimethylacrylate, ethyl 2-pentenoate, ethyl 2-fluoroacrylate, ethyl 3,3-dichloroacrylate, ethyl 4,4-dichlorocrotonate, ethyl 2-dichloromethylacrylate, ethyl 5,5-dichloropenta-2,4-dienate, ethyl 3-benzylacrylate, ethyl 2-benzylacrylate, ethyl 2-(p-methylbenzyl)acrylate, ethyl 2-(p-methoxybenzyl)acrylate, ethyl 2-(p-chlorobenzyl)acrylate, ethyl cinnamate, ethyl p-methylcinnamate, ethyl p-methoxycinnamate, ethyl p-chlorocinnamate, i-propyl acrylate, i-propyl crotonate, i-propyl methacrylate, i-propyl tiglate, i-propyl 3,3-dimethylacrylate, i-propyl 2-pentenoate, i-propyl 2-fluoroacrylate, i-propyl 3,3-dichloroacrylate, i-propyl 4,4-dichlorocrotonate, i-propyl 2-dichloromethylacrylate, i-propyl 5,5-dichloropenta-2,4-dienate, i-propyl 3-benzylacrylate, i-propyl 2-benzylacrylate, i-propyl 2-(p-methylbenzyl)acrylate, i-propyl 2-(p-methoxybenzyl)acrylate, i-propyl 2-(p-chlorobenzyl)acrylate, i-propyl cinnamate, i-propyl p-methylcinnamate, i-propyl p-methoxycinnamate, i-propyl p-chlorocinnamate, t-butyl acrylate, t-butyl crotonate, t-butyl methacrylate, t-butyl tiglate, t-butyl 3,3-dimethylacrylate, t-butyl 2-pentenoate, t-butyl 2-fluoroacrylate, t-butyl 3,3-dichloroacrylate, t-butyl 4,4-dichlorocrotonate, t-butyl 2-dichloromethylacrylate, t-butyl 5,5-dichloropenta-2,4-dienate, t-butyl 3-benzylacrylate, t-butyl 2-benzylacrylate, t-butyl 2-(p-methylbenzyl)acrylate, t-butyl 2-(p-methoxybenzyl)acrylate, t-butyl 2-(p-chlorobenzyl)acrylate, t-butyl cinnamate, t-butyl p-methylcinnamate, t-butyl p-methoxycinnamate, t-butyl p-chlorocinnamate, phenyl acrylate, phenyl crotonate, phenyl methacrylate, phenyl tiglate, phenyl 3,3-dimethylacrylate, phenyl 2-pentenoate, phenyl 2-fluoroacrylate, phenyl 3,3-dichloroacrylate, phenyl 4,4-dichlorocrotonate, phenyl 2-dichloromethylacrylate, phenyl 5,5-dichloropenta-2,4-dienate, phenyl 3-benzylacrylate, phenyl 2-benzylacrylate, phenyl 2-(p-methylbenzyl)acrylate, phenyl 2-(p-methoxybenzyl)acrylate, phenyl 2-(p-chlorobenzyl)acrylate, phenyl cinnamate, phenyl p-methylcinnamate, phenyl p-methoxycinnamate, phenyl p-chlorocinnamate, and the like. Acrylates and methacrylates are preferred in the present invention.

The hydroxy compound of the formula (2) used in the present invention include an alkyl alcohol, an aralkyl alcohol or an aryl alcohol, all of which may be substituted.

Examples of the substituents on the alkyl group of the alkyl alcohol which may be substituted include a group selected from an alkoxy group, phenoxy group, a cyano group, a dialkylamino group, a halogen atom, a furyl group, a tetrahydrofurfuryl group, an ethylenoxide group, a hydroxy group and the like.

Examples of the alkyl alcohol which may be substituted include methyl alcohol, ethyl alcohol, n-propyl alcohol, isopropyl alcohol, n-butyl alcohol, s-butyl alcohol, t-butyl alcohol, n-pentyl alcohol, neopentyl alcohol, amyl alcohol, n-hexyl alcohol, n-octyl alcohol, n-decyl alcohol, cyclohexyl alcohol, 2-ethylhexyl alcohol, ethylene glycol, 2-dimethylaminoethanol, 2-diethylaminoethanol, 2-cyanoethanol, 2-methoxyethanol, 2-ethoxyethanol, 2-phenoxyethanol, furfuryl alcohol, tetrahydrofurfuryl alcohol, glycidol, chloromethyl alcohol, dichloromethyl alcohol, trichloromethyl alcohol, bromomethyl alcohol, dibromomethyl alcohol, tribromomethyl alcohol, fluoromethyl alcohol, difluoromethyl alcohol, trifluoromethyl alcohol, fluoroethyl alcohol, difluoroethyl alcohol, trifluoroethyl alcohol, tetrafluoroethyl alcohol, pentafluoroethyl alcohol, perfluoropropyl alcohol, hexafluoroisopropyl alcohol, perfluorobutyl alcohol, perfluoropentyl alcohol, perfluorohexyl alcohol, perfluorooctyl alcohol, and perfluorodecyl alcohol.

Examples of the substituents on the aralkyl group of the aralkyl alcohol which may be substituted include an alkyl group, an alkoxy group, a phenoxy group, a nitro group, a cyano group, a halogen atom and the like.

Examples of the aralkyl group of the aralkyl alcohol include the same aralkyl group as described for $R_1$, $R_2$ or $R_3$ and an anthracenyl group.

Specific examples of the aralkyl alcohol which may be substituted include: benzyl alcohol, 3-phenoxybenzyl alcohol, 2-hydroxy-2-(3-phenoxyphenyl)ethane nitrile, (2-methylphenyl)methyl alcohol, (3-methylphenyl)methyl alcohol, (4-methylphenyl)methyl alcohol, (2,3-dimethylphenyl)methyl alcohol, (2,4-dimethylphenyl) methyl alcohol, (2,5-dimethylphenyl)methyl alcohol, (2,6-dimethylphenyl)methyl alcohol, (3, 4-dimethylphenyl) methyl alcohol, naphthylmethyl alcohol, anthracenylmethyl alcohol, 1-phenylethyl alcohol, 1 (1-naphthyl)ethyl alcohol, 1-(2-naphthyl)ethyl alcohol,

- haloaralkyl alcohols derived from the above-listed alcohols by substituting hydrogen with halogen such as fluorine, chlorine and bromine,
- alkoxyaralkyl alcohols derived from the haloaralkyl alcohols described above by optionally replacing their halogen atom with a (C1–C4) alkoxy group such as a methoxy group, an ethoxy group, a n-propoxy group, an i-propoxy group, a n-butoxy group, a s-butoxy group, a t-butoxy group or the like,
- cyanoaralkyl alcohols and
- nitroaralkyl alcohols.

Examples of the aryl alcohols which may be substituted include phenol, l-naphthol, 2-naphthol and the like, and ones derived therefrom with their aromatic ring substituted with the alkyl group, the alkoxyl group, the halogen atom, or the like as described above.

Preferred hydroxy compounds (2) are secondary or primary alcohols because of their reactivity, and especially preferred are primary alcohols.

The amount of the hydroxy compound (2) is usually one mol or more per mol of the unsaturated ester (1), and may be used excessively if desired. It may also be used as a solvent. Conversely, the unsaturated ester may be used excessively and can be used as a solvent, if necessary. In general, unreacted starting materials can be recovered after the reaction, for example, by distillation.

The reaction of the unsaturated ester (1) and the hydroxy compound (2) in the presence of the lanthanoide metal alkoxide is usually carried out in an atmosphere of an inert gas such as argon and nitrogen. The reaction can be conducted under atmospheric pressure, elevated pressure or reduced pressure, and preferably carried out under atmospheric pressure or reduced pressure.

The transesterification reaction is preferably promoted by continuously removing an alcohol resulting from the reaction, thereby the equilibrium of the transesterification reaction is shifted to the desired product. The removal of the said by-product alcohol can be conducted by distillation or the like in case the resulting alcohol has a lower boiling point than that of the alcohol compound of the formula (2), alternatively the by-product alcohol can be removed as an azeotrope with an appropriate solvent selected from those listed below.

The reaction can be carried out in the presence or absence of solvent. Examples of the solvent used include halogenated hydrocarbons such as dichloromethane, chloroform and 1,2-dichloroethane, aliphatic hydrocarbons such as hexane, heptane, octane and nonane, aromatic hydrocarbons such as benzene, toluene, xylene and chlorobenzene, ethers such as diethyl ether and tetrahydrofuran.

The reaction temperature is not particularly limited, and preferably ranges from 0 to 150° C., more preferably ranges from 10 to 100° C. Mild conditions are preferred for controlling side reactions.

The catalyst can be removed from the unsaturated ester (3) formed by the reaction, for example, by washing with water or acidic water. The ester can be readily isolated from the reaction mixture by distillation or the like, if necessary.

EXAMPLES

The following examples explain the present invention in detail, but the invention is not limited thereto.

Example 1

Into a 20 mL eggplant type flask which had been filled with nitrogen gas, 0.04 g (0.1 mmol) of triisopropoxy samarium(III), 1.72 g (20 mmol) of methyl acrylate and 5.23 g (40 mmol) of 1-octanol were placed, and stirred at 25° C. for 2 hours. The gas chromatography analysis of the reaction mixture indicated that the yield of 1-octyl acrylate was 50% (Selectivity based on the consumed methyl acrylate was 72%).

Example 2

Into a 20 mL eggplant type flask which had been filled with nitrogen gas, 8.2 mg (0.03 mmol) of triisopropoxy lanthanum(III), 511.8 mg (6 mmol) of methyl acrylate and 1.554 g (12 mmol) of 1-octanol were placed, and stirred at 25° C. for 2 hours. The gas chromatography analysis of the reaction mixture indicated that the yield of 1-octyl acrylate was 50% (Selectivity based on the consumed methyl acrylate was 81%).

Example 3

1-Octyl acrylate was obtained in a yield of 52% by carrying out a reaction in the same manner as Example 2 except for using 11.6 mg of t-butoxy lanthanum(III) in place of 8.2 mg of triisopropoxy lanthanum(III) (Selectivity based on the consumed methyl acrylate was 80%).

Comparative Example 1

1-Octyl acrylate was obtained in a yield of 1% by carrying out a reaction in the same manner as Example 2 except for using 7.2 mg of dibutyltin oxide in place of 8.2 mg of triisopropoxy lanthanum(III).

Comparative Example 2

1-octyl acrylate was obtained in a yield of 1% by carrying out a reaction in the same manner as Example 2 except for using 12.8 mg of triphenyltin hydroxide in place of 8.2 mg of triisopropoxy lanthanum(III)

Example 4

Into a 20 mL eggplant type flask which had been filled with nitrogen gas, 39 mg (0.11 mmol) of tri-t-butoxy lanthanum(III), 1143.8 mg (11.4 mmol) of methyl methacrylate and 3.03 g (23 mmol) of 2-ethylhexyl alcohol were placed, and stirred at 25° C. for 2 hours. The gas chromatography analysis of the reaction mixture indicated that the yield of 2-ethylhexyl methacrylate was 67% (Selectivity based on the consumed methyl methacrylate was 98%).

Comparative Example 3

2-Ethylhexyl methacrylate was obtained in a yield of 19% by carrying out a reaction in the same manner as Example 4 except for using 7.5 mg of sodium ethoxide in place of 39 mg of tri-t-butoxy lanthanum(III) (Selectivity based on the consumed methyl methacrylate was 99%).

Example 5

Into a 20 mL eggplant type flask which had been filled with nitrogen gas, 11.4 mg (0.03 mmol) of tri-t-butoxy lanthanum(III), 578.1 mg (5.8 mmol) of methyl methacrylate and 1.19 g (12 mmol) of tetrahydrofurfuryl alcohol were placed, and stirred at 25° C. for 2 hours. The gas chromatography analysis of the reaction mixture indicated that the yield of tetrahydrofurfuryl methacrylate was 32% (Selectivity based on the consumed methyl methacrylate was 93%).

Comparative Example 4

Tetrahydrofurfuryl methacrylate was obtained in a yield of 15% by carrying out a reaction in the same manner as Example 5 except for using 2.1 mg of sodium ethoxide in place of 11.4 mg of tri-t-butoxy lanthanum(III) (Selectivity based on the consumed methyl methacrylate was 70%).

Example 6

Into a 20 mL eggplant type flask which had been filled with nitrogen gas, 30.4 mg (0.10 mmol) of tri-i-propoxy lanthanum(III), 2.06 g (20.6 mmol) of methyl methacrylate and 1.18 g (10 mmol) of 2-diethylaminoethanol were placed, and stirred at 100° C. for 4 hours. The gas chromatography analysis of the reaction mixture indicated that the yield of 2-diethylaminoethyl methacrylate was 66% (Selectivity based on the consumed methyl methacrylate was 93%).

Comparative Example 5

Diethylaminoethyl methacrylate was obtained in a yield of 47% by carrying out a reaction in the same manner as Example 6 except for using 6.3 mg of sodium ethoxide in place of 30.4 mg of tri-i-propoxy lanthanum(III) (Selectivity based on the consumed methyl methacrylate was 92%).

Comparative Example 6

Diethylaminoethyl methacrylate was obtained in a yield of 38% by carrying out a reaction in the same manner as Example 6 except for using 23.6 mg of dibutyltinoxide in place of 30.4 mg of tri-i-propoxy lanthanum(III) (Selectivity based on the consumed methyl methacrylate was 88%).

Example 7

Into a 20 mL eggplant type flask which had been filled with nitrogen gas, 48.5 mg (0.15 mmol) of tri-i-propoxy lanthanum(III), 5.91 g (59.0 mmol) of methyl methacrylate and 0.93 g (15 mmol) of ethyleneglycol were placed, and stirred at 100° C. for 4 hours. The gas chromatography analysis of the reaction mixture indicated that the yield of ethyleneglycol dimethacrylate was 46% (Selectivity based on the consumed methyl methacrylate was 48%).

Comparative Example 7

Into a 20 mL eggplant type flask which had been filled with nitrogen gas, 21.8 mg (0.40 mmol) of sodium methoxide, 3.12 g (31.1 mmol) of methyl methacrylate and 0.48 g (7.7 mmol) of ethyleneglycol were placed, and stirred at 100° C. for 4 hours. The gas chromatography analysis of the reaction mixture indicated that the yield of ethyleneglycol dimethacrylate was 22% (Selectivity based on the consumed methyl methacrylate was 23%).

Comparative example 8

Methacrylate ester was not obtained by carrying out a reaction in the same manner as example 7 except for using 36.1 mg of dibutyltinoxide in place of 48.5 mg of tri-i-propoxy lanthanum(iii).

What is claimed is:

1. A process for producing an unsaturated ester of the formula (3):

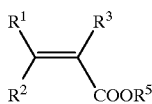

(3)

wherein $R^1$, $R^2$ and $R^3$ independently represent a hydrogen atom, a halogen atom, an alkyl group which may be substituted, an alkenyl group which may be substituted, an aralkyl group which may be substituted or an aryl group which may be substituted and $R^5$ represents:
an alkyl group which may be substituted with an alkoxy group, a phenoxy group, a cyano group, a dialkylamino group, a cycloalkyl group or a halogen atom,
an aralkyl group which may be substituted with an alkyl group, an alkoxy group, a phenoxy group, a nitro group, a cyano group or a halogen atom, or
an aryl group which may be substituted with an alkyl group, an alkoxy group or a halogen atom, which comprises subjecting an unsaturated ester of the formula (1):

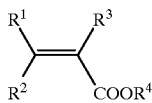

(1)

wherein $R^1$, $R^2$ and $R^3$ have the same meaning as defined above and $R^4$ represents an alkyl group having 1 to 10 carbon atoms which may be substituted or a phenyl group which may be substituted, to a transesterification reaction with a hydroxy compound of the formula (2):

(2)

wherein $R^5$ has the same meaning as defined above, in the presence of a lanthanoide metal alkoxide.

2. The preparation process according to claim 1 wherein the lanthanoide metal is La or Sm.

3. The preparation process according to claim 1, wherein the lanthanoide metal alkoxide is $La(OiPr)_3$, $La(OtBu)_3$ or $Sm(OiPr)_3$.

4. The preparation process according to any one of claims 1, 2 or 3, wherein $R^4$ in the unsaturated ester of the formula (1) is a methyl or ethyl.

5. The preparation process according to any one of claims 1, 2 or 3, wherein the unsaturated ester of the formula (1) is an acrylic ester.

6. The preparation process according to any one of claims 1, 2 or 3, wherein the unsaturated ester of the formula (1) is a methacrylic ester.

7. The preparation process according to any one of claims 1, 2 or 3, wherein the hydroxy compound of the formula (2) is a primary or secondary alcohol.

8. The preparation process according to any one of claims 1, 2 or 3, wherein the hydroxy compound of the formula (2) is a primary alcohol.

9. The process according to any one of claims 1, 2 or 3, wherein said lanthanoide alkoxide compound is a recovered lanthanoide alkoxide compound.

10. The process according to any one of claims 1, 2 or 3, wherein said lanthanoide alkoxide compound is a microencapsulated lanthanoide metal alkoxide.

11. The process according to any one of claims 1, 2 or 3, wherein said lanthanoide metal alkoxide is a lanthanoide metal alkoxide that is supported on a polymer, silica gel or active carbon.

* * * * *